(12) United States Patent
Mastel

(10) Patent No.: US 6,440,109 B1
(45) Date of Patent: Aug. 27, 2002

(54) MEDICAL LASER VACUUM CHAMBER SYSTEM

(76) Inventor: David R. Mastel, 10271 Mescalero Rd., Phelan, CA (US) 92371

( * ) Notice: Subject to any disclaimer, the term of this patent is extended or adjusted under 35 U.S.C. 154(b) by 0 days.

(21) Appl. No.: 09/558,635

(22) Filed: Apr. 26, 2000

(51) Int. Cl.[7] ............................................... A61M 35/00
(52) U.S. Cl. ...................................... 604/313; 604/294
(58) Field of Search ................................. 604/313, 176, 604/36, 199, 268, 289, 290, 294, 295, 319; 606/4, 10, 11, 15; 607/90, 91

(56) References Cited

U.S. PATENT DOCUMENTS

| | | | | |
|---|---|---|---|---|
| 4,963,134 A | * | 10/1990 | Backscheider et al. | ..... 604/319 |
| 5,345,935 A | * | 9/1994 | Hirsch et al. | ........... 600/387 X |
| 5,645,081 A | * | 7/1997 | Argenta et al. | ........... 602/42 X |
| 5,941,873 A | * | 8/1999 | Korenfeld | ............... 604/313 X |

* cited by examiner

Primary Examiner—Anhtuan T. Nguyen
(74) Attorney, Agent, or Firm—Donn K. Harms

(57) ABSTRACT

A device for removing air and all airborne contaminants from a laser surgery site, such as an eye surface undergoing laser surgery. Laser surgery creates a plume of smoke, vapor and other contaminants that are adverse to the health of the surgeon and other operating room staff. The device includes a tubular chamber having an upstanding wall which is sized to fit over and around tissue at the surgery site. A first annular channel in the wall is exposed along a lower end of the chamber and is connected to a first tube for extracting air. This will hold the chamber in place by the vacuum between tissue and channel. A second annular channel in the wall is connected to a second tube for extracting air to a full vacuum from the second channel. Small holes or slits communicate between the chamber interior and the second channel so that air is pulled from the chamber through the holes and out the second tube. A raised edge is provided along part of the chamber upper edge. A third, larger, extraction tube is connected to a hole in the edge so that air can be pulled across the entire upper end of the chamber and out through the third tube, catching all contaminants before they can escape from the chamber.

14 Claims, 2 Drawing Sheets

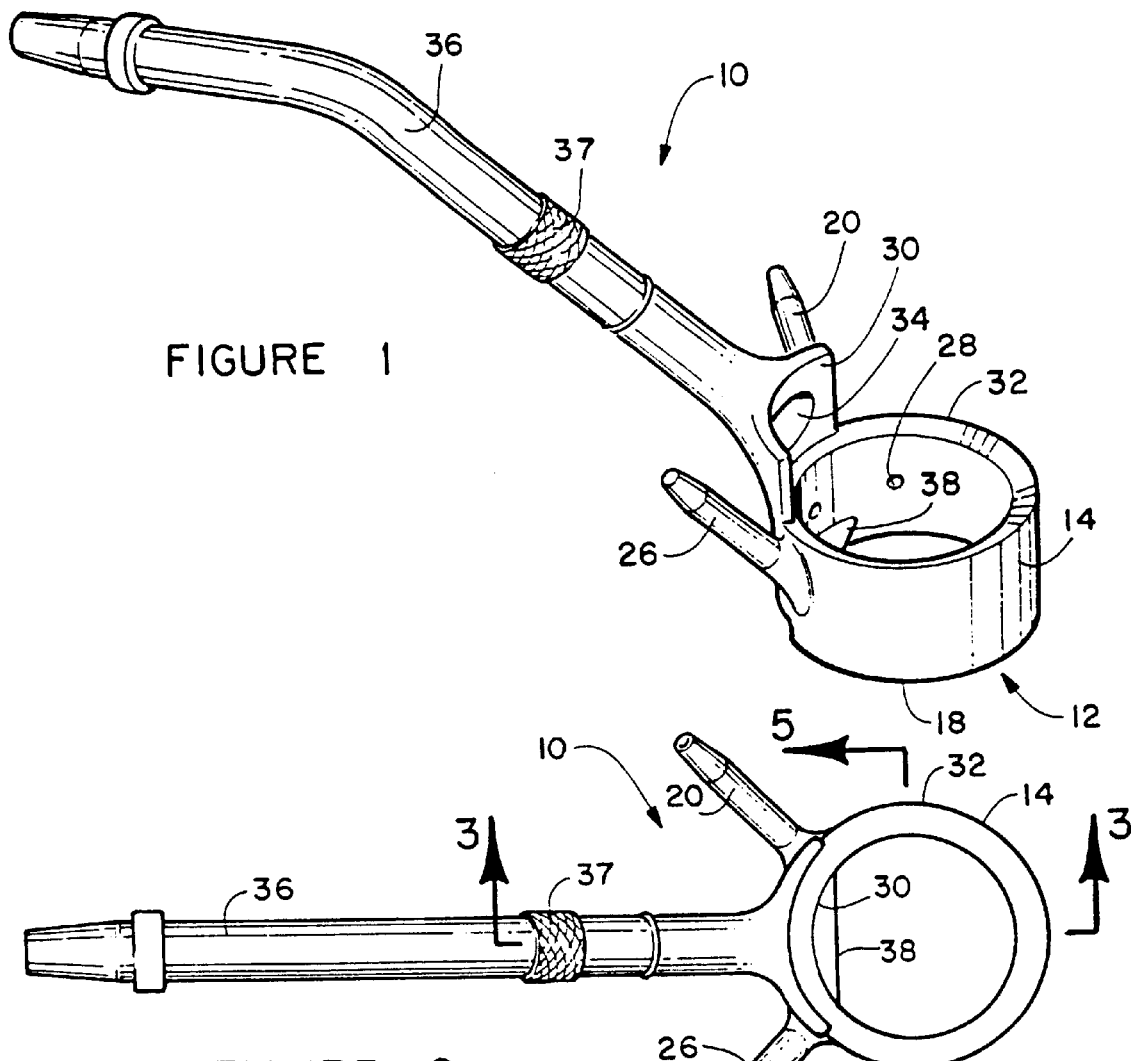
FIGURE 1
FIGURE 2
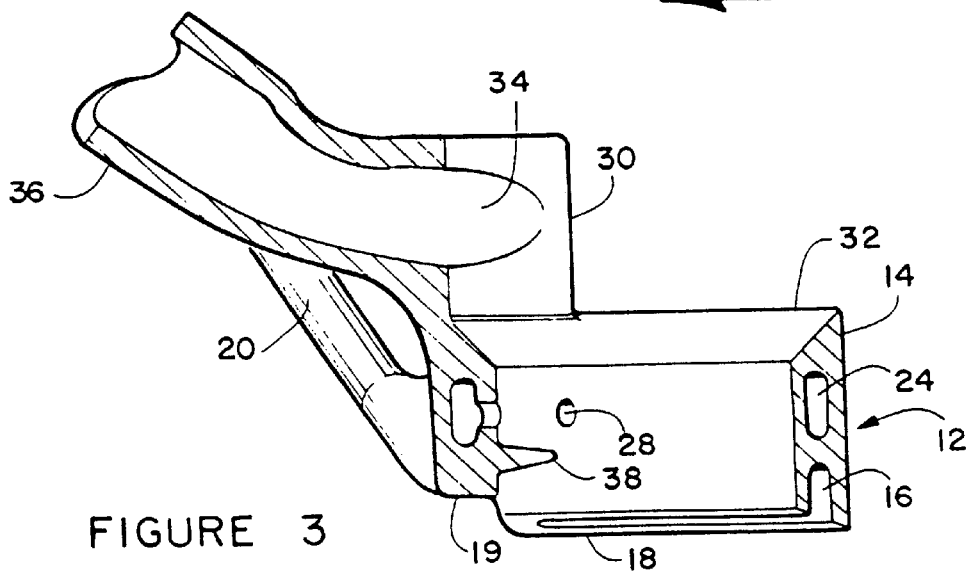
FIGURE 3

MEDICAL LASER VACUUM CHAMBER SYSTEM

FIELD OF THE INVENTION

This invention relates to devices for removing airborne contaminants created various types of surgery, in particular contaminants volatilized during laser surgery.

BACKGROUND OF THE INVENTION

A number of different surgical techniques produce contaminants such as fumes, vapors and airborne particulates that are potentially harmful to surgeons medical staff. These contaminants may be produced during cautery, sawing, drilling and other procedures. Particularly severe problems occur during medical laser ablation, such as in excimer laser photoablation used in refractive eye surgery, removal of lesions, cosmetic surgery, etc.

Excimer laser photoablation has been a particularly rapidly growing technique in refractive eye surgery. This surgery results in a plume of smoke and particles at the surgery site. There is great concern about potentially debilitating and possibly lethal illnesses to surgeons and staff who are exposed routinely to the laser plume by inhalation of airborne byproducts that may include viruses, bacteria and pathogenic microbes. Also, chronic coughs, fatigue, nausea and other conditions affect many surgeons and staff members who undergo long-term exposure to this environment.

When an excimer laser is fired at the surface of an eye, typically at an ultraviolet wavelength of 193 nm the surface layer is volatilized through the breakdown of covalent bonds in organic material. An odor of burnt skin arises as particulates of various sizes and shapes are ejected into the environment. Often suction hoses are placed near the photoablation site to draw off a continuous stream of air entraining the particulates. However, these suction hoses are very loud, draw large volumes of air into the surgical field which potentially introduces pathogens into the field while not intercepting all of the particulates, including infectious viruses and bacteria.

A surgical laser smoke plume evacuator is described by Korenfeld in U.S. Pat. No. 5,941,873. This device uses an elongated tube having a central region bent into an approximately circular loop. The loop is placed in contact with an eye, surrounding the surgical field. A number of small holes penetrate the inner side of the loop. Air is drawn into the small holes by a vacuum system connected to the tube ends. Two of these loops may be stacked and used simultaneously. This arrangement will collect and remove a significant portion of the smoke plume resulting from laser impacts on the eye. However, because the loop is relative large in diameter, is not precisely circular and the collecting holes are relatively close to the eye surface, not all of the contaminants resulting from the laser impact may be collected. Particles that are ejected with some upward velocity may well escape the suction system.

Further, the evacuator of this Korenfeld patent may tend to slide over the surface of the eye during surgery, disturbing the surgeon performing the highly critical surgery and potentially damaging the eye. While including teeth along the lower edge are described in one embodiment, the teeth alone may be insufficient to prevent slipping, and could scratch the eye surface if moved.

Thus, there is a continuing need for improved devices and systems for assuring substantially complete capture and removal of all contaminants resulting from laser photoablation surgery and other surgical procedures that result in the release of particulates and vapors into the air around the surgical field and that will stay in place during surgery.

SUMMARY OF THE INVENTION

The above-noted problems, and others, are overcome in accordance with this invention by a vacuum chamber device including a tube having a surrounding wall, and inner and outer surfaces, a lower end for placing in contact with the surface of a laser surgery site such as an eye and an exposed, open upper end through which a laser beam enters to engage the surgical surface.

A first approximately annular channel is provided within the wall along the lower wall end, open to the lower end. A first air extraction tube penetrates the tube outer surface and communicates with the first chamber. When a vacuum is drawn on the first channel with the lower edge in contact with the surgical site, the resulting fixed vacuum in the first channel will securely hold the tube in place. Preferably, a portion of the tube lower edge is recessed to allow air to enter the tube along the eye surface.

A second annular channel is provided in the wall spaced from the upper and lower ends. A plurality of small holes extend through the inner wall surface in communication with the second channel. A second extraction tube penetrates the outer wall surface and communicates with the second channel. When a vacuum is drawn on the second extraction tube and second channel, air is extracted from within the tube, carrying with it an vapors, particulates, etc. formed by the laser operation.

A raised edge, preferably conforming to the tube shape, extends above a predetermined portion of the tube upper edge. A relatively large opening in the raised edge connects to a third extraction tube which when connected to a vacuum extraction system to draw a large volume of air across the top of the tube. This will assure that no vapors, particulates or the like can escape from the system and enter the surgical environment.

In certain surgical techniques, a tissue flap is formed, with a small tissue hinge connecting the flap to the adjacent tissue. A small ledge is preferably provided extending inwardly of the tube inner surface to protect such a hinge from exposure to the laser beam.

BRIEF DESCRIPTION OF THE DRAWING

Details of the invention, and of preferred embodiments thereof, will be further understood upon reference to the drawing, wherein:

FIG. 1 is a perspective view of the vacuum chamber device of this invention;

FIG. 2 is a top plan view of the vacuum chamber device;

FIG. 3 is a section view taken on line 3—3 in FIG. 2;

DETAILED DESCRIPTION OF PREFERRED EMBODIMENTS

Referring to FIG. 1, there is seen the vacuum chamber device 10 of this invention. A tubular chamber 12 is sized to fit around a site for laser surgery, such as an eye. While a circular cross section, as shown, is preferred, any other suitable cross sections may be used, if desired. Chamber 12 includes a surrounding wall 14 having upper and lower ends and inner and outer surfaces. While the dimensions of chamber 12 may vary, for eye surgery a wall height of from about 0.2 to 0.5 inches and a chamber width of from about 0.35 to 0.75 inches are preferred. Chamber 12 may be manufactured in any suitable manner. While any suitable material may be used for device 10, a metal such as stainless steel is preferred. The various chambers, detailed below such as stainless steel, by any conventional method, such as chemical milling, diffusion bonding, welding or brazing parts together, etc. If desired, the device may be made from a plastic material, such as by injection molding.

Figure 5:
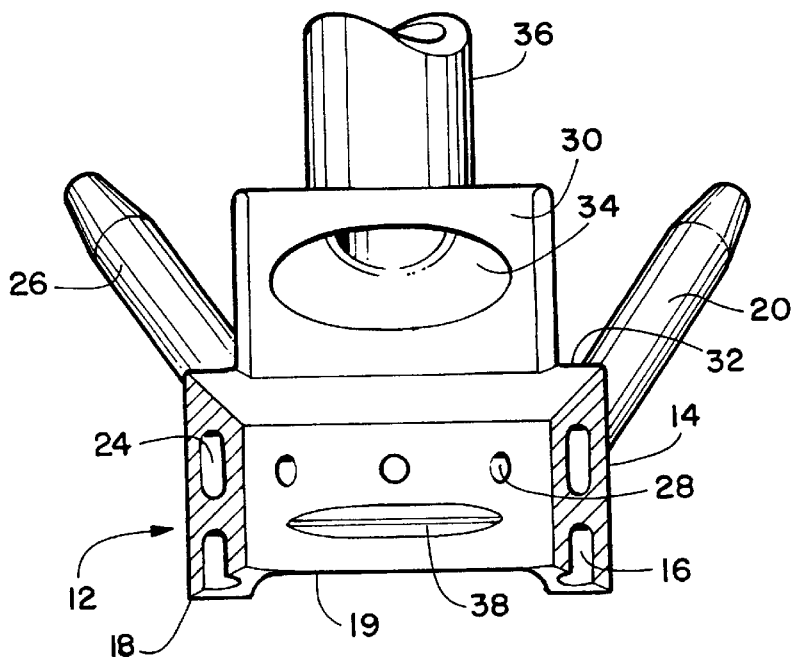
FIG. 5 is a section view of the vacuum chamber device taken on line 5—5 in FIG. 2.

As best seen in FIGS. 3 and 5, a first annular channel 16 is provided within wall 14, adjacent to the lower chamber end. First annular channel 16 is exposed at the lower end 18. A first extraction tube 20 is secured to wall 18, such as by welding and communicates with first annular channel 16 though an opening (not seen) through wall 18.

Figure 6:
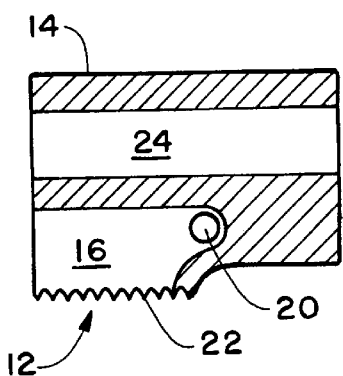
FIG. 6 is a detail view illustrating inclusion of teeth along the device lower end.

When air is extracted through first extraction tube 20, a vacuum is created in the first annular channel 16 and tissue against which device 10 is placed, holding the device tightly against the tissue. If desired, in order to further prevent movement of device 10 along tissue at a surgical site, fine teeth 22 as seen in FIG. 6 may be provided.

Figure 4:
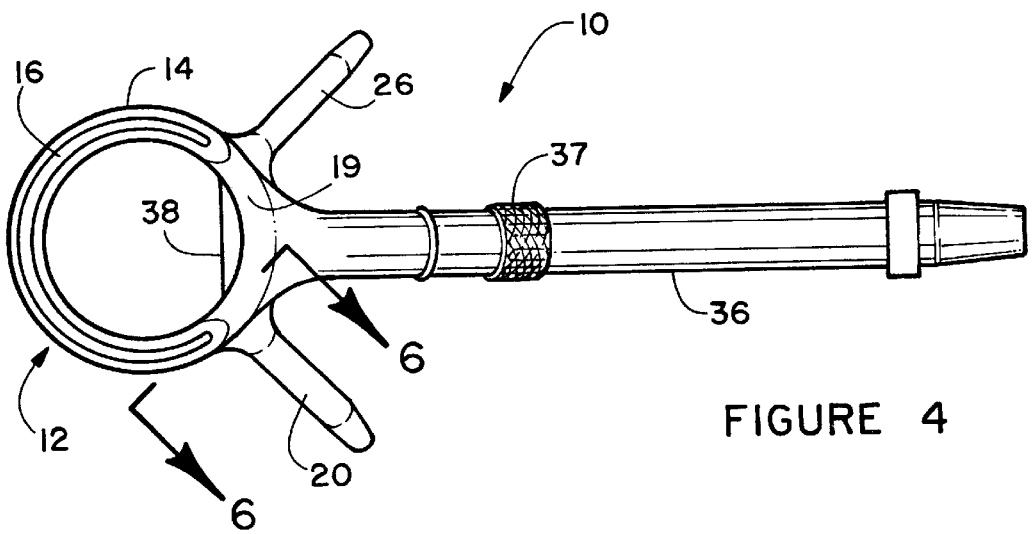
FIG. 4 is a bottom plan view of the vacuum chamber device.

Preferably, a portion 19 of the lower end 18 of wall 14 is cut back slightly to allow ambient air to enter chamber 12 and aid in removal of contaminants as seen in FIGS. 3–5. This opening also allows the flap that is formed in some types of eye surgery to fit under the cut out region to avoid applying heavy pressure to the flap. In some cases, light pressure on the flap is desirable. The lower, otherwise open, edge of first annular channel 16 is closed along this recessed area. Preferably, the recessed area 19 extends from about 10 to 25 per cent of the circumference of lower end 18.

A second annular channel 24 within wall 14 is spaced above the lower first channel 16. A second extraction tube 26 communicates through wall 14 with second annular channel 24. A plurality of small apertures 28 communicate between second annular channel 24 and the interior of chamber 12. Apertures 28 may be round or slit-like, as desired. In operation, air is extracted through second extraction tube 26, causing air and any airborne contaminants to flow through apertures 28. Apertures 28 may have any suitable size and may be located any suitable distance above the chamber lower end 18. For best results when used in laser eye surgery, from about 2 to 7 round apertures 28 having diameters of from about 0.005 to 0.1 inch are provided, located at least about 0.1 inch above lower end 18. Where apertures 28 are in the form of slits, typical dimensions include from about 0.003 by 0.4 inch.

A raised edge 30 extends above upper end 32 of chamber 12. Typically, edge 30 extends around from about 10 to 30 percent of the upper end circumference and has a height of from about 0.15 to 1 inch above upper end 32. Preferably, the upper edge of raised end extends about 0.16 inch above tube 36. A hole 34 through raised edge 30 communicates with a third extraction tube 36. Extraction of air through tube 36 will cause a rapid flow of air across chamber upper end 32, assuring that all contaminants will be trapped and carried away before they can exit chamber 12. While third extraction tube 36 may have any suitable diameter, preferably the cross sectional area is preferably at least about 2 times the cross sectional area of all apertures 28. Two vacuum sources are preferably used, one connected to tubes 26 and 36 and the other to tube 20, to assure that there is sufficient suction in channel 16 to hold the device against the eye surface while assuring that a considerable air flow is provided across the chamber upper end 32. Raised and or roughened areas 37 may be provided along tube 36 to aid in holding and moving device 10. For clearing the slit lamp beams produced into the chamber and best viewing by the surgeon it is preferred that wall 14 around upper end 32 is tapered from higher along the outside to lower along the inside.

In some types of surgery, the surgeon cuts a flap of tissue such that a hinge is retained at one side so that the flap may be folded back, then returned and secured in the original position. To protect such a hinge from exposure to the laser light, inclusion of a small ledge 38 along one side of the inner surface of chamber 12 is preferred.

Any conventional vacuum pumps or the like may be used to extract air from the three air extraction tubes. Generally, three separate pumps each connected to one of tubes 20, 22 and 36 are preferred. Also, conventional valves could be used at each pump to vary the air flow and end vacuum in each of those tubes.

The relative vacuum produced by velocity of air flow in each of tubes 20, 26 and 36 may be varied in any suitable manner. For example, For example, relatively greater air flow through tube 36 will create a high speed sweep across the top of chamber 12. If desired, air can be introduced through tube 26, to be swept away by the vacuum generated by tube 36.

Other applications, variations and ramifications of the present invention will occur to those skilled in the art. Those are intended to be included within the scope of this invention, as defined in the appended claims.

I claim:

1. A vacuum chamber device for use in laser surgery, which comprises:
   a tubular chamber having a surrounding wall, inner and outer surfaces and upper and lower ends;
   a first channel within said wall along said lower end and open to said lower end;
   a first air extraction tube penetrating said wall and communicating with said first channel;
   a second channel within said wall adjacent to said upper end;
   a plurality of apertures penetrating through said inner surface and communicating with said second channel;
   a second air extraction tube penetrating said wall and communicating with said second channel; and
   a raised edge extending from a predetermined portion of said upper end;
   a third air extraction tube penetrating said raised edge;
   whereby air extracted through said first air extraction tube will cause said chamber to be held against a surface contiguous to said lower edge, air extracted through said second air extraction tube will cause air and any contaminants to be removed from within said chamber and air extracted through said third extraction tube will cause air and any contaminants to be pulled across said upper end and removed.

2. The vacuum chamber device according to claim 1 wherein a predetermined portion of said lower end is recessed to avoid excessive pressure on a surgically produced tissue flap.

3. The vacuum chamber device according to claim 1 further including a ledge on said inner surface spaced above said lower edge and extending into said chamber.

4. The vacuum chamber device according to claim 1 wherein said apertures are located at least about 0.12 inch above said lower end.

5. The vacuum chamber device according to claim 1 wherein said third extraction tube has a cross sectional area at least about 3 times the total cross sectional area of said first and second extraction tubes.

6. The vacuum chamber device according to claim 1 further including a plurality of teeth a portion of said lower end extending away from said lower end.

7. The vacuum chamber device according to claim 1 wherein said upper end of said wall is tapered downwardly from said outer surface towards said inner surface.

8. The vacuum chamber device according to claim 1 wherein said raised edge extends about 0.16 inch above said third extraction tube.

9. A vacuum chamber device for use in laser surgery, which comprises:

a tubular chamber having a surrounding wall, inner and outer surfaces and upper and lower ends;

said lower end recessed over a predetermined distance;

a plurality of teeth on said lower end, other than where said lower end is recessed, said teeth extending away from said lower end;

a first channel within said wall along said lower end and open to said lower end;

a first air extraction tube penetrating said wall and communicating with said first channel;

a second channel within said wall adjacent to said upper end;

a plurality of apertures penetrating through said inner surface and communicating with said second channel;

a second air extraction tube penetrating said wall and communicating with said second channel; and a raised edge extending from a predetermined portion of said upper end;

a third air extraction tube penetrating said raised edge;

whereby air extracted through said first air extraction tube will cause said chamber to be held against a surface contiguous to said lower edge, air extracted through said second air extraction tube will cause air and any contaminants to be removed from within said chamber and air extracted through said third extraction tube will cause air and any contaminants to be pulled across said upper end and removed.

10. The vacuum chamber device according to claim 9 wherein said apertures are located at least about 0.12 inch above said lower end.

11. The vacuum chamber device according to claim 9 wherein said third extraction tube has a cross sectional area at least about 3 times the total cross sectional area of said first and second extraction tubes.

12. The vacuum chamber device according to claim 9 further including a plurality of teeth a portion of said lower end extending away from said lower end.

13. The vacuum chamber device according to claim 9 wherein said upper end of said wall is tapered downwardly from said outer surface towards said inner surface.

14. The vacuum chamber device according to claim 9 wherein said raised edge extends about 0.16 inch above said third extraction tube.

* * * * *